United States Patent
Gumudavelli et al.

(10) Patent No.: US 12,357,578 B2
(45) Date of Patent: Jul. 15, 2025

(54) IBUPROFEN AND FAMOTIDINE TABLET

(71) Applicant: APPCO PHARMA LLC, Piscataway, NJ (US)

(72) Inventors: Peddanna Gumudavelli, Piscataway, NJ (US); Kishore Kumar Konda, Quthbullapur Mandal (IN); Srinivasa R. Paruchuri, Piscataway, NJ (US); M. V. K. Satish, Quthbullapur Mandal (IN); Y. V. Raghava Chowdary, Quthbullapur Mandal (IN)

(73) Assignee: APPCO PHARMA LLC, Piscataway, NJ (US)

( * ) Notice: Subject to any disclaimer, the term of this patent is extended or adjusted under 35 U.S.C. 154(b) by 0 days.

(21) Appl. No.: 17/497,660

(22) Filed: Oct. 8, 2021

(65) Prior Publication Data
US 2022/0125732 A1    Apr. 28, 2022

Related U.S. Application Data

(60) Provisional application No. 63/105,022, filed on Oct. 23, 2020.

(51) Int. Cl.
*A61K 9/28* (2006.01)
*A61K 9/20* (2006.01)
*A61K 31/192* (2006.01)
*A61K 31/426* (2006.01)

(52) U.S. Cl.
CPC .......... *A61K 9/2886* (2013.01); *A61K 9/2009* (2013.01); *A61K 9/2027* (2013.01); *A61K 9/2054* (2013.01); *A61K 9/2095* (2013.01); *A61K 31/192* (2013.01); *A61K 31/426* (2013.01)

(58) Field of Classification Search
CPC .. A61K 9/2886; A61K 9/2009; A61K 9/2027; A61K 9/2054; A61K 9/2095; A61K 31/192; A61K 31/426
See application file for complete search history.

(56) References Cited

U.S. PATENT DOCUMENTS

| | | | |
|---|---|---|---|
| 2003/0069255 A1* | 4/2003 | Plachetka | A61P 29/00 514/255.04 |
| 2003/0086967 A1* | 5/2003 | Morita | A61K 31/165 424/465 |
| 2003/0091643 A1* | 5/2003 | Friesen | A61K 9/10 514/249 |
| 2008/0254102 A9* | 10/2008 | Nogami | A61P 1/04 424/443 |
| 2014/0186439 A1* | 7/2014 | Xu | A61P 29/00 514/370 |

* cited by examiner

*Primary Examiner* — Robert A Wax
*Assistant Examiner* — Olga V. Tcherkasskaya
(74) *Attorney, Agent, or Firm* — William D. Hare; McNeely, Hare & War, LLP

(57) ABSTRACT

The invention relates to a solid, pharmaceutical composition in compressed tablet form. The tablet comprises an ibuprofen core tablet, a pair of protective barriers and a famotidine outermost coating. The ibuprofen core tablet comprises ibuprofen and one or more pharmaceutically acceptable excipients selected from disintegrants, diluents, fillers, binders, glidants and lubricants. The pair of protective barrier coatings surround the ibuprofen core tablet. The first coating comprises a methacrylic acid and ethyl acrylate copolymer, a surfactant, and hydroxypropylmethylcellulose. The second coating comprises hydroxypropylmethylcellulose, and a plasticizer. The outermost coating comprises famotidine, polyvinyl alcohol and a plasticizer.

18 Claims, No Drawings

IBUPROFEN AND FAMOTIDINE TABLET

FIELD OF THE INVENTION

The present invention relates to tablets of ibuprofen and famotidine that are formulated to address the incompatibility of famotidine and ibuprofen.

BACKGROUND OF THE INVENTION

Ibuprofen is a non-steroidal anti-inflammatory drug (NSAID) and is chemically known as (±)-2-(p-isobutylphenyl) propionic acid. Its chemical formula is $C_{13}H_{18}O_2$ and molecular weight is 206.28. Ibuprofen is a white powder that is very slightly soluble in water (<1 mg/mL) and readily soluble in organic solvents such as ethanol and acetone. Its structural formula is:

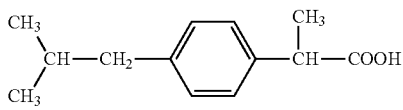

NSAIDs, including ibuprofen are known to cause gastritis, dyspepsia, and gastric and duodenal ulceration. Gastric and duodenal ulceration result from impaired mucosal integrity, which in turn is a result of ibuprofen-mediated inhibition of prostaglandin synthesis. Gastric and duodenal ulceration causes problems for those individuals who must take ibuprofen for an extended period of time, e.g., patients suffering from rheumatoid arthritis and osteoarthritis.

It is known that the risk of developing gastric or duodenal ulceration can be reduced by co-therapy with the famotidine, which is chemical known as N'-(aminosulfonyl)-3-[[[2-[di-aminomethylene)amino]-4-thiazlyl]methyl]thio]propanimideamide with a chemical formula of $C_8H_{15}N_7O_2S_3$ and a molecular weight of 337.45. Famotidine is a white to pale yellow crystalline compound that is freely soluble in glacial acetic acid, slightly soluble in methanol, very slightly soluble in water, and practically insoluble in ethanol. Its structural formula is:

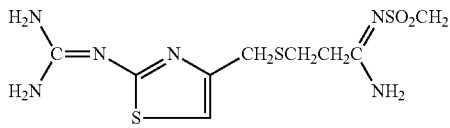

Famotidine blocks the action of the histamine type 2 (H2) receptor, leading to a reduction of acid secretion in the stomach. Reducing stomach acid with famotidine during treatment with certain nonsteroidal anti-inflammatory drugs is known to decrease the incidence of gastrointestinal ulcers.

An ibuprofen-famotidine fixed dosage combination tablet is marketed as Duexis® and contains 800 mg of ibuprofen and 26.6 mg of famotidine. Although the prescribing information for the ibuprofen-famotidine tablets (sold under the trademark Duexis® tablets) does not disclose the structure of the tablet, the tablets include ibuprofen and famotidine as the active ingredients. The inactive ingredients are: microcrystalline cellulose, anhydrous lactose, croscarmellose sodium, colloidal silicon dioxide, magnesium stearate, purified water, povidone, titanium dioxide, polyethylene glycol, polysorbate 80, polyvinyl alcohol, hypromellose, talc, FD&C Blue, #2/Indigo Carmine Aluminum Lake and FD&C Blue #1/Brilliant Blue FCF Aluminum Lake.

Ibuprofen and famotidine co-therapy is described in U.S. Pat. Nos. 8,067,033; 8,067,451; 8,309,127; 8,318,202; 8,449,910; and 8,501,228. The specification of the '451 Patent describes a solid oral dosage form having a first portion containing ibuprofen and a second portion containing famotidine in which the first portion completely surrounds the second portion or the second portion completely surrounds the first portion. A barrier layer is disposed between the first and second portions. The ibuprofen and famotidine are released into solution rapidly. The specification also describes one embodiment as being an ibuprofen-containing core portion surrounded by a famotidine-containing layer and a barrier layer being interposed between the core portion and famotidine-containing layer.

The specification of the '451 Patent describes the barrier layer as being a layer in the unit dosage form that is interposed between the ibuprofen-containing compartment (e.g., an ibuprofen core or coated ibuprofen particles) and the famotidine-containing compartment (e.g., famotidine-containing coating or coated famotidine particles). The specification explains that the barrier layer retards the release of API by less than 5 minutes. The specification also explains that there is an incompatibility between ibuprofen and famotidine that is overcome by formulating the ibuprofen and famotidine in separate compartments of the dosage form. The specification also describes a rapid release of the famotidine and ibuprofen with the oral dosage forms releasing both the ibuprofen and famotidine occurring or beginning to occur at about the same time, i.e., within 5 minutes of each other.

The '451 Patent states that the famotidine layer is applied over the barrier coat and can be applied by compression, spray coating, or other methods. As a preferred embodiment, the famotidine layer is applied by spray coating a formulation containing famotidine and excipients such as polymers, plasticizers, and the like. As one example, the famotidine is combined with Opadry II and spray coated over the ibuprofen core or barrier layer.

The present inventors have successfully designed and developed a stable pharmaceutical formulation of ibuprofen and famotidine in a single tablet that includes an ibuprofen core, a barrier layer over the ibuprofen core and an outer famotidine coating.

SUMMARY OF THE INVENTION

Broadly, the present invention relates to a pharmaceutical composition containing ibuprofen and famotidine, in combination with at least one pharmaceutically acceptable excipient. The invention also relates to methods of making a pharmaceutical composition containing ibuprofen and famotidine. The at least one excipient may include conventional excipients, such as one or more diluents/fillers, binders, disintegrants, glidants and lubricants. The composition contains an ibuprofen core, a barrier coating or coatings over the ibuprofen core, and an outer famotidine coating.

In a first aspect, the invention relates to a solid, pharmaceutical composition in compressed tablet form. The tablet comprises an ibuprofen core tablet, a pair of protective barriers and a famotidine outermost coating.

The ibuprofen core tablet comprises ibuprofen and one or more pharmaceutically acceptable excipients selected from disintegrants, diluents, fillers, binders, glidants and lubricants.

The pair of protective barrier coatings surround the ibuprofen core tablet. A first coating comprises a methacrylic acid and ethyl acrylate copolymer, a surfactant, and hydroxypropylmethylcellulose. A second coating comprises hydroxypropylmethylcellulose, and a plasticizer.

The outermost coating comprises famotidine, polyvinyl alcohol and a plasticizer.

Embodiments of the composition include one or more of the following features. For example, the first coating may be in contact with the ibuprofen core tablet and the second coating surrounds the first coating. In another embodiment the second coating may be in contact with the ibuprofen core tablet and the first coating surrounds the second coating.

The surfactant in the first coating may be one or more of Poloxamer and sodium lauryl sulfate. The first coating may further include one or more of talc, titanium dioxide, Poloxamer, calcium silicate, sodium bicarbonate and sodium lauryl sulfate.

The plasticizer in the second coating may be polyethylene glycol. The polyethylene glycol may be polyethylene glycol 400. The second coating may further include titanium dioxide.

The outermost coating may further include a glidant and the outermost coating may comprise talc as the glidant. The outermost coating may include polyethylene glycol as the plasticizer. The polyethylene glycol may be polyethylene glycol 3350. The outermost coating also can include a colorant, such as FD&C Blue No. 1 to provide an aesthetic look.

In one aspect, the tablet may be configured such that it does not release ibuprofen from the composition within five minutes when the tablet is subjected to dissolution testing in a pH 7.2 phosphate buffer, 900 ml, and a paddle rotation speed of 50 rpm. In another aspect, the tablet may be configured such that is does not release ibuprofen from the composition within fifteen minutes when the tablet is subjected to dissolution testing in a pH 4.5 acetate buffer, 900 ml, and a paddle rotation speed of 50 rpm.

In one specific embodiment, the solid, pharmaceutical may configured with the core tablet comprising about 800 mg of ibuprofen, about 45 mg to about 120 mg of intragranular disintegrant, diluents and fillers, about 15 mg to about 35 mg binder, about 50 to about 120 mg of extragranular disintegrant, and about 15 mg to about 55 mg of extragranular glidant and lubricant. The first coating may comprise about 2 mg to about 20 mg of hydroxypropylmethylcellulose, about 8 mg to about 40 mg of methacrylic acid and ethyl acrylate copolymer, about 3 mg to about 15 mg glidant, about 2 mg to about 10 mg opacifier, about 0.1 mg to about 1.0 mg surfactant, and optional anticaking agent and alkalizer. The second coating may comprise about 10 mg to about 60 mg of hydroxypropylmethylcellulose, about 6 mg to about 30 mg opacifier and about 1.5 mg to about 6.0 mg of plasticizer. The outermost coating may comprise about 26.6 mg famotidine, about 15 mg to about 70 mg of polyvinyl alcohol, about 4.0 mg to about 20.0 mg of plasticizer, and about 6 mg to about 35 mg glidant.

In one embodiment, the outermost coating includes a colorant, such as FD&C Blue No. 1 to provide an aesthetic look. The colorant may be present in an amount of about 0.1 mg to about 0.5 mg per tablet.

In another specific embodiment, the core tablet comprises about 800 mg of ibuprofen, about 45 mg to about 120 mg of intragranular of a combination of microcrystalline cellulose and lactose, about 15 mg to about 35 mg of povidone, about 50 to about 120 mg of extragranular croscarmellose sodium, and about 15 mg to about 55 mg of a combination of extragranular colloidal silicon dioxide, talc and magnesium stearate.

The first coating may comprise about 2 mg to about 20 mg hydroxypropylmethylcellulose, about 8 mg to about 40 mg of methacrylic acid and ethyl acrylate copolymer, about 3 mg to about 15 mg of talc, about 2 mg to about 10 mg titanium dioxide, about 1 mg to about 5.0 mg of a combination of poloxamer and sodium lauryl sulfate, and about 2.0 mg to 15.0 mg of a combination of an optional anticaking agent and alkalizer.

The second coating may comprise about 10 mg to about 60 mg hydroxypropylmethylcellulose, about 6 mg to about 30 mg of titanium dioxide and about 1.5 mg to about 6.0 mg of polyethylene glycol.

The outermost coating may comprise about 26.6 mg famotidine, about 15 mg to about 70 mg of polyvinyl alcohol, about 4.0 mg to about 20.0 mg of polyethylene glycol, and about 6 mg to about 35 mg of talc.

In one embodiment, the outermost coating may further include a colorant, such as FD&C Blue No. 1 to provide an aesthetic look. In this embodiment, the colorant may be present in an amount of about 0.1 mg to about 0.5 mg per tablet.

In another general aspect, the invention relates to a process for preparing a solid, pharmaceutical composition of ibuprofen and famotidine in the form of a compressed tablet. The process comprises the following steps:

A first step of preparing granules of ibuprofen and one or more pharmaceutically acceptable excipients selected from intragranular disintegrants, diluents, fillers and binders.

A second step of blending the granules with one or more extragranular disintegrants, glidants and lubricants;

A third step of compressing the blend to form ibuprofen core tablets/

A fourth and a fifth step of preparing coated ibuprofen core tablets by coating the ibuprofen core tablets with a pair of protective barrier coatings. The first coating comprises a methacrylic acid and ethyl acrylate copolymer, a surfactant, and hydroxypropylmethylcellulose, and the second coating comprises hydroxypropylmethylcellulose, and a plasticizer.

A fifth step of coating the coated ibuprofen core tablets with an outermost coating comprising famotidine, polyvinyl alcohol and a plasticizer.

Embodiments of the process may include one or more of the following features. In one embodiment of the process, the first coating may be in contact with the ibuprofen core tablet and the second coating surrounds the first coating. In another embodiment of the process, the second coating is in contact with the ibuprofen core tablet and the first coating surrounds the second coating.

In a specific embodiment of the process, the ibuprofen core tablet comprises about 800 mg of ibuprofen, about 45 mg to about 120 mg of intragranular disintegrant, diluents and fillers, about 15 mg to about 35 mg binder, about 50 to about 120 mg of extragranular disintegrant, and about 15 mg to about 55 mg of extragranular glidant and lubricant.

In this embodiment, the first coating comprises about 2 mg to about 20 mg of hydroxypropylmethylcellulose, about 8 mg to about 40 mg of methacrylic acid and ethyl acrylate copolymer, about 3 mg to about 15 mg of glidant, about 2 mg to about 10 mg of opacifier, about 0.1 mg to about 1.0 mg of surfactant, and optional anticaking agent and alkalizer. The second coating comprises about 10 mg to about 60 mg of hydroxypropylmethylcellulose, about 6 mg to about 30 mg of opacifier and about 1.5 mg to about 6.0 mg of plasticizer.

In this embodiment, the outermost coating comprises about 26.6 mg of famotidine, about 15 mg to about 70 mg of polyvinyl alcohol, about 4 mg to about 20 mg of plasticizer, and about 6 mg to about 35 mg of glidant.

In another embodiment, the outermost coating may further include a colorant, such as FD&C Blue No. 1 to provide an aesthetic look. The colorant may be present in an amount of about 0.1 mg to about 0.5 mg per tablet.

In another specific embodiment, the core tablet comprises about 800 mg of ibuprofen, about 45 mg to about 120 mg of intragranular of a combination of microcrystalline cellulose and lactose, about 15 mg to about 35 mg of povidone, about 50 to about 120 mg of extragranular croscarmellose sodium, and about 15 mg to about 55 mg of a combination of extragranular colloidal silicon dioxide, talc and magnesium stearate.

In this specific embodiment, the first coating comprises about 2 mg to about 20 mg of hydroxypropylmethylcellulose, about 8 mg to about 40 mg of methacrylic acid and ethyl acrylate copolymer, about 3 mg to about 15 mg of talc, about 2 mg to about 10 mg of titanium dioxide, about 1 mg to about 5 mg of a combination of poloxamer and sodium lauryl sulfate, and about 2.0 mg to 15.0 mg of a combination of an optional anticaking agent and alkalizer. The second coating comprises about 10 mg to about 60 mg of hydroxypropylmethylcellulose, about 6 mg to about 30 mg of titanium dioxide and about 1.5 mg to about 6.0 mg of polyethylene glycol.

In this specific embodiment, the outermost coating comprises about 26.6 mg of famotidine, about 15 mg to about 70 mg of polyvinyl alcohol, about 4.0 mg to about 20.0 mg of polyethylene glycol, and about 6 mg to about 35 mg of talc. The outermost coating may further include an optional colorant, such as FD&C Blue No. 1. The colorant may be present in an amount of about 0.1 mg to about 0.5 mg per tablet.

DETAILED DESCRIPTION

According to the literature, it is known that famotidine is incompatible with ibuprofen. To understand the extent of incompatibility and rate of degradation, a reference tablet of ibuprofen and famotidine was produced using wet granulation and then tested for stability. The formulation details are provided in Table 1, Reference Example 1:

TABLE 1

| Reference Example 1 | |
| --- | --- |
| Ingredient | Unit formula (mg) |
| Ibuprofen | 800.00 |
| Famotidine | 26.60 |
| Microcrystalline Cellulose | 147.50 |
| Lactose Anhydrous | 147.50 |
| Povidone K 30 | 30.00 |
| Purified water | Q.S. |
| Croscarmellose sodium | 80.00 |
| Colloidal Silicon dioxide | 10.00 |
| Magnesium Stearate | 5.00 |
| Total Tablet weight | 1,246.6 |

A mixture of ibuprofen, microcrystalline cellulose, and lactose was granulated using an aqueous dispersion of Povidone K30. The resulting granules then were blended with famotidine, croscarmellose sodium and colloidal silicon dioxide. The blend of granules then were lubricated with magnesium stearate and compressed to form an ibuprofen and famotidine tablet. As should be evident, the granules containing intragranular ibuprofen are in direct contact with the extragranular famotidine.

The resulting tablets were stored for fifteen days at 60° C. in an open container to evaluate the tablets under accelerated conditions. Tables 2 and 3 report the famotidine- and ibuprofen-related compounds after storage for fifteen days at these conditions.

TABLE 2

Famotidine-related impurities

| | | | Formulation Approach: Ibuprofen and Famotidine Core Tablets Condition: |
| --- | --- | --- | --- |
| Famotidine related compounds | Proposed Spec limits | Initial-RT | 60° C. 2 weeks Open |
| Famotidine Amidine (RC-A) | NMT 0.2% | ND | 0.66* |
| Famotidine dimer (RC-B) | NMT 0.3% | 0.005 | 0.09 |
| Famotidine Sulfamoyl propanamide (RC-C) | NMT 0.5% | 0.04 | 15.31* |
| Famotidine Propanamide (RC-D) | NMT 0.5% | 0.04 | 12.28* |
| Famotidine disulfide (RC-E) | NMT 0.3% | 0.01 | 0.20 |
| Famotidine Propionic acid (RC-F) | NMT 0.5% | 0.01 | 5.02* |
| Single max unspecified imp | NMT 0.2% | 0.039 | 1.63* |
| Total Impurity | 1.5% | 0.29 | 50.7* |

*Exceeds proposed specification limit

TABLE 3

Ibuprofen-related impurities

| | | | Formulation Approach Ibuprofen and Famotidine Core Tablets Condition |
| --- | --- | --- | --- |
| Ibuprofen related compounds | Proposed Spec limits | Initial-RT | 60° C. 2 weeks Open |
| Impurity J | NMT 0.2% | 0.01 | 0.03 |
| Single max unspecified imp | NMT 0.2% | 0.03 | 0.05 |
| Total Impurity | 1.5% | 0.09 | 0.10 |

The stability data reported in Table 2 shows that the famotidine is rapidly and extensively degraded when in intimate contact with ibuprofen. However, the stability data reported in Table 3 shows that the ibuprofen was found to be stable under the same conditions. The data in Tables 2 and 3 provide a baseline for improving stability of tablets of ibuprofen and famotidine.

To address the stability of the famotidine when in the presence of the ibuprofen, further formulations were developed by applying a protective barrier coating between the ibuprofen core and the famotidine active layer coating.

In general, the formulations developed contain an ibuprofen core in combination with at least one pharmaceutically acceptable excipient, at least one barrier coating around the ibuprofen core, and an outermost famotidine coating. The at least one excipient in the core may include conventional excipients, such as one or more disintegrants, binders, diluents/fillers, glidants and lubricants.

In one variation of the formulation, the solid, pharmaceutical formulation may be in compressed tablet form that consists of (i) an ibuprofen core tablet, (ii) a pair of protective barrier coatings surrounding the core tablet, and (iii) an outermost famotidine coating. The core tablet consists of the ibuprofen and one or more pharmaceutically acceptable excipients selected from the group consisting of disintegrants, diluents, fillers, binders, glidants and lubricants. The pair of protective barrier coatings surrounding the ibuprofen core tablet are in the form of a first coating that consists of a methacrylic acid and ethyl acrylate copolymer, a surfactant, and hydroxypropylmethylcellulose, and a second coating that consists of hydroxypropylmethylcellulose and a plasticizer. The outermost coating consists of famotidine, polyvinyl alcohol and a plasticizer. It should be understood that the first coating can be in contact with the ibuprofen core tablet and the second coating surrounds the first coating. It also should be understood that the reverse is suitable with the second coating being in contact with the ibuprofen core tablet and the first coating surrounds the second coating.

In another variation of the formulation, the solid, pharmaceutical formulation may be in compressed tablet form that consists essentially of (i) an ibuprofen core tablet and pharmaceutical excipients to deliver the ibuprofen, (ii) an outermost famotidine coating and pharmaceutical excipients to deliver the famotidine; and (iii) a pair of protective barrier coatings surrounding the core tablet to protect the ibuprofen and famotidine from each other due to their incompatibility, and/or to delay the release of the ibuprofen relative to the famotidine. The core tablet consists essentially of the ibuprofen and one or more pharmaceutically acceptable excipients selected from the group consisting of disintegrants, diluents, fillers, binders, glidants and lubricants. The pair of protective barrier coatings surrounding the ibuprofen core tablet are in the form of a first coating that consists essentially of a methacrylic acid and ethyl acrylate copolymer, a surfactant, and hydroxypropylmethylcellulose, and a second coating that consists essentially of hydroxypropylmethylcellulose and a plasticizer. The outermost coating consists essentially of famotidine, polyvinyl alcohol and a plasticizer. It should be understood that the first coating can be in contact with the ibuprofen core tablet and the second coating surrounds the first coating. It also should be understood that the reverse is suitable with the second coating being in contact with the ibuprofen core tablet and the first coating surrounds the second coating.

The methacrylic acid and ethyl acrylate copolymer may be replaced with or supplemented with other polymer systems that provide suitable functionality. For example, such polymer systems include methacrylic acid, methyl methacrylate (1:1) (Eudragit L100) and methacrylic acid, methyl methacrylate (1:2) (Eudragit S100). The amounts of methacrylic acid, methyl methacrylate (1:1) (Eudragit L100) and methacrylic acid, methyl methacrylate (1:2) (Eudragit S100) can be the same or similar amounts as set out herein for the methacrylic acid and ethyl acrylate copolymer.

Protective Barrier Coating

A first protective barrier coating material can be Acryl-EZE II (a methacrylic acid and ethyl acrylate copolymer system, described in detail below in Table 8), a methacrylic acid, methyl methacrylate (1:1) polymer system (e.g., Eudragit L100) and a methacrylic acid, methyl methacrylate (1:2) polymer system (e.g., Eudragit S100). The first protective barrier coating material can be about 2% to about 8% by weight of the core tablet weight. A preferred coating weight build up is about 3% of the core tablet weight.

A second protective barrier coating material can be a hydroxypropylmethylcellulose-based film coating system such as marketed as Opadry. One particularly suitable Opadry is the Opadry Complete film coating system 03B28796. The coating system is provided as a ready mix powder and further contains titanium dioxide and polyethylene glycol. Its composition is set out in Table 9. The second protective barrier coating material can be about 2% to about 8% by weight of the weight of the core tablet with a first protective coating layer. A preferred coating weight build up is about 4% of the weight of the core tablet and first protective coating layer.

Outermost Coating

The outermost coating material can be a polyvinyl alcohol-based film coating system such as marketed as Opadry. One particularly suitable Opadry is the Opadry Clear Coating system 85F190000. The coating system is provided as a ready mix powder and further contains talc and polyethylene glycol. Its composition is set out in Table 10. The outermost coating material can be about 5% to about 12% by weight of the weight of the core tablet and two protective barrier coatings. A preferred coating weight build up is about 7-8% of the weight of the core tablet and two protective barrier coatings.

Disintegrant

A disintegrant is a substance which helps the ibuprofen core break up once ingested. Preferably the total weight of the core is comprised of about 3 to about 15 wt % disintegrant, about 2 to about 15 wt % disintegrant, or about 2 to about 8 wt % disintegrant. The disintegrant may be present intragranularly and/or extragranularly. If the disintegrant is present intragranularly and extragranularly, the disintegrant may be the same or different.

Suitable disintegrants include alginic acid (sold under the trademarks KELACID™, PROTACID™, SATIALGINE H8™), calcium phosphate, tribasic (sold under the trademarks TRI-CAFOS™, TRI-CAL WG™, TRI-TAB™), carboxymethylcellulose calcium (sold under the trademarks ECG 505™, NYMCEL ZSC™), carboxymethylcellulose sodium (sold under the trademarks AKUCELL™, AQUASORB™, BLANOSE™, FINNFIX™, NYMCEL TYLOSE CB™), colloidal silicon dioxide (sold under the trademarks AEROSIL™, CAB-O-SIL™, CAB—O-SIL™-5P™, WACKER HDK™), croscarmellose sodium (sold under the trademarks AC-DI-SOL™, EXPLOCEL™, NYMCEL ZSX™, PHARMACEL XL™, PRIMEL-LOSE™, SOLUTAB™, VIVASOL™), crospovidone (sold under the trademarks KOLLIDON CL™, KOLLIDON CL-M™, POLYPLASDONE XL™, POLYPLASDONE XL-10™), docusate sodium, guar gum (sold under the trademarks GALACTOSOL™, MEPROGAT™, MEYPRODOR™, MEYPROFIN™, MEYPROGUAR™), low substituted hydroxypropyl cellulose, magnesium aluminum silicate (sold under the trademarks CARRISORB™, GELSORB™, MAGNABITE™, NEUSILIN™, PHARMSORB™, VEEGUM™), methylcellulose (sold under the trademarks BENECEL™, CULMINAL MC™, METHOCEL™, METOLOSE™), microcrystalline cellulose (sold under the trademarks AVICEL PH™, CELEX™, CELPHERE™, CEOLUS KG™, EMCOEL™, ETHISPHERES™, FIBROCEL™, PHARMACEL™, TABULOSE™, VIVAPUR™), povidone (sold under the trademarks KOLLIDON™, PLASDONE™), sodium alginate (sold under the trademarks KELCOSOL™, KELTONE™, PROTANAL™), sodium starch glycolate (sold under the trademarks EXPLOTAB™, PRIMOJEL™, VIVASTAR P™), polacrilin potassium (sold under the trademarks AMBERLITE IRP88™), silicified microcrystalline cellulose (sold under the trademarks PROSOLV™), starch (sold under the trademarks AYTEX P™, FLUFTEX W™, INSTANT PURE-COTE™, MELOJEL™, MERITENA™, PAYGEL 55™, PERFECTAMYL D6PH™, PURE-BIND™, PURE-CORE™, PURE-COTE™, PURE-DENT™, PURE-GEL™, PURE-SET™, PURITY 21™, PURITY 826™, TABLET WHITE™), or pre-gelatinized starch (sold under the trademarks INSTANSTARCH™, LYCATAB C™, LYCATAB PGS™, MERIGEL™, NATIONAL 78-1551™, PHARMA-GEL™, PREJEL™, SEPISTAB ST 200™, SPRESS B820™, STARCH 1500 G™, TABLITZ™, UNIPURE LD™ and UNIPURE WG220™), or mixtures thereof.

Preferred disintegrants are super-disintegrants such as croscarmellose sodium, crospovidone, low substituted hydroxypropyl cellulose, microcrystalline cellulose, carboxymethylcellulose sodium, carboxymethylcellulose calcium and sodium starch glycolate. A particularly suitable disintegrant is croscarmellose sodium. When the disintegrant is croscarmellose sodium, the total weight of the ibuprofen core is comprised of about 3 to about 15 wt % disintegrant.

Binder

A binder is a substance that holds the components of the composition together in the required composition form. Preferably the total weight of the composition is comprised of about 0.5 to about 14 wt % binder, more preferably about 5 to about 9 wt % binder.

Suitable binders for inclusion in the composition of the invention include acacia, alginic acid (sold under the trademarks KELACID™, PROTACID™, SATIALGINE H8™), carbomer (sold under the trademarks ACRITAMER™, CARBOPOL™, PEMULEN™, ULTREZ™), carboxymethylcellulose sodium (sold under the trademarks AKU-CELL™, AQUASORB™, BLANOSE™, FINNFIX™, NYMCEL™, TYLOSE™), ceratonia (sold under the trademark MEYPROFLEUR™), cottonseed oil, dextrin (sold under the trademarks AVEDEX™, CALOREEN™, CRYSTAL GUM™, PRIMOGRAN W™), dextrose (sold under the trademarks CARIDEX™, DEXTROFM™, LYCEDEX PF™, ROFEROSE™, TABFME D-IOO™), gelatin (sold under the trademarks CRYOGEL™, INSTAGEL™, SOLU-GEL™), guar gum (sold under the trademarks GALACTO-SOL™, MEPROGAT™, MEYPRODOR™, MEYPROFM™, MEYPROGUAR™), hydrogenated vegetable oil type I (sold under the trademarks AKOFINE™, LUBRI-TAB™, STEROTEX™, DYNASAN P[OMICRON]O™, SOFTISAN 154™, HYDROCOTE™, LIPOVOL™, HS-K™, STEROTEX HM™), hydroxyethyl cellulose (sold under the trademarks ALCORAMNOSAM™, CELLO-SIZE™, IDRORAMNOSAN™, LIPORAMNOSAN™, NATROSOL™, TYLOSE PHA™), hydroxyethylmethyl cellulose (sold under the trademarks CULMINAL™, TYLOPUR MH™, TYLOPUR MHB™, TYLOSE MB™, TYLOSE MH™, TYLOSE MHB™), hydroxypropyl cellulose (sold under the trademarks KLUCEL™, METHO-CEL™ NISSO HPC™), low substituted hydroxypropyl cellulose, hypromellose (sold under the trademarks BENECEL MHPC™, METHOCEL™, METOLOSE™, PHARMACOAT™, SPECTRACEL 6™, SPECTRACEL 15™, TYLOPUR™), magnesium aluminium silicate (sold under the trademarks CARRISORB™, GELSORB™, MAGNA-BITE™, NEUSILIN™, PHARMSORB™, VEEGUM™), maltodextrin (sold under the trademarks C*DRY MD™, GLUCIDEX™, GLUCODRY™, LYCATAB DSH™, MALDEX™, MALTAGRAN™, MALTRIN™, MALTRIN QD™, PASELLI MD 10 PHIM, STAR-DRI™), maltose (sold under the trademark ADVANTOSE 100™), methylcellulose (sold under the trademarks (BENECEL™, CULMINAL MC™, METHOCEL™, METOLOSE™), microcrystalline cellulose (sold under the trademarks (AVICEL PH™, CELEXV™, CELPHERE™, CEOLUS KG™, EMCOCEL™, ETHISPHERES™, FIBROCEL™, PHARMACEL™, TABULOSE™, VIVAPUR™), polydextrose (sold under the trademark LITESSE™), polyethylene oxide (sold under the trademark POLYOX™), polymethacrylates (sold under the trademarks EASTACRYL 30D™, EUDRAGIT™, KOLLICOAT MAE 30D™, KOLLICOAT MAE 30DP™), povidone (sold under the trademarks KOLLIDON™, PLASDONE™), sodium alginate (sold under the trademark KELCOSOL™, KELTONE™, PROTANAL™), starch (sold under the trademarks AYTEX P™, FLUFTEX W™, INSTANT PURE-COTE™, MELOJEL™, MERITENA PAYGEL 55™, PERFECTAMYL D6PH™, PURE-BIND™, PURE-COTE™, PURE-DENT™, PURE-GEL™, PURE-SET™, PURITY 21™, PURITY 826™, TABLET WHITE™), pregelatinised starch (sold under the trademarks INSTASTARCH™, LYCATAB C™, LYCATAB PGS™, MERIGEL™, NATIONAL 78-1551™, PHARMA-GEL™, PREJEL™, SEPISTAB ST 200™, SPRESS B820™, STARCH 1500 G™, TABLITZ™, UNIPURE LD™, UNIPURE WG 220™), stearic acid (sold under the trademarks CRODACID™, EMERSOL HYSTRENE™, INDUSTRENET, KORTACID 1895™, PRISTERENE™), sucrose and zein, or mixtures thereof.

Preferred binders include povidone, hypromellose, hydroxypropyl cellulose, methylcellulose, ethyl-cellulose, pregelatinised maize starch and gelatine. The most preferred binder is povidone. When the binder is povidone, the total weight of the composition is preferably comprised of about 0.5 to about 14 wt % binder.

Diluent/Filler

The term 'filler' and the term 'diluent' are herein used interchangeably. It is known that, in general, the term 'filler' is used in the context of capsular formulations and the term 'diluent' in tablet formulations. Fillers fill out the size of a composition, making it practical to produce and convenient for the consumer to use.

The composition may comprise a diluent/filler, which may be present in an amount up to about 20 wt % of the total weight of the ibuprofen core.

When present in the composition, suitable fillers include for example calcium carbonate (sold under the trademarks BARCROFT™, CAL-CARB™, CALCIPURE™, DESTAB™, MAGGRAN™, MILLICARB™, PHARMACARB™, PRECARB™, STURCAL™, VIVAPRES CA™), calcium phosphate, dibasic anhydrous (sold under the trademarks A-TAB™, DI-CAFOS A-N™, EMCOMPRESS ANHYDROUS™, FUJICALIN™), calcium phosphate, dibasic dihydrate (sold under the trademarks CAFOS™, CALIPHARM™, CALSTAR™, DI-CAFOS™, EMCOMPRESS™), calcium phosphate tribasic (sold under the trademarks TRI-CAFOS™, TRI-CAL WG™, TRI-TAB™), calcium sulphate (sold under the trademarks DESTAB™, DRIERITE™, SNOW WHITE™, CAL-TAB™, COMPACTROL™, USG TERRA ALBA™), cellulose powdered (sold under the trademarks ARBOCEL™, ELCEMA™, SANACEL™, SOLKA-FLOC™), silicified microcrystalline cellulose (sold under the trademark PROSOLV™), cellulose acetate, compressible sugar (sold under the trademarks DI-PAC™), confectioner's sugar, dextranes (sold under the trademarks CANDEX™, EMDEX™), dextrin (sold under the trademarks AVEDEX™, CALOREEN™, CRYSTAL GUM™, PRIMOGRAN W™), dextrose (sold under the trademarks CARIDEX™, DEXTROFIN™, LYCADEX PF™, ROFEROSE™, TAB FINE DT-IOO™), fructose (sold under the trademarks ADVANTOSE™, FRUCTAMYL™, FRUCTOFIN™, KRYSTAR™), kaolin (sold under the trademarks LION™, SIM 90™), lactitol (sold under the trademarks FINLAC ACX™, FINLAC DC™, FINLAC MCX™), lactose (sold under the trademarks AERO FLO 20™, AERO FLO 65™, ANHYDROX™, CAPSULAC™, FAST-FLO™, FLOWLAC™, GRANULAC™, INHALAC™, LACTOCHEMIM, LACTOHALE™, LACTOPRESS™, MICROFINE™, MICROTOSE™, PHARMATOSE™, PRISMA LAC™, RESPITOSE™, SACHELAC™, SORBOLAC™, SUPER-TAB™, TABLETTOSE™, WYNDALE™, ZEPAROX™), magnesium carbonate, magnesium oxide (sold under the trademark (MAGGRAN MO™), maltodextrin (sold under the trademarks C*DRY MD™, GLUCIDEX™, GLUCODRY™, LYCATAB DSH™, MALDEX™, MALTAGRAN™, MALTRIN™, MALTRIN QD™ PASELLI MD 10 PHIM, STARDRI™), maltose (sold under the trademark ADVANTOSE 100™), mannitol (sold under the trademarks MANNOGEM™, PEARLITOL™), microcrystalline cellulose (sold under the trademarks AVICEL PH™, CELEX™, CELPHERE™, CEOLUS KG™, EMCOCEL™, ETHISPHERES™, FIBROCEL™, PHARMACEL™, TABULOSE™, VIVAPUR™), polydextrose (sold under the trademark LITESSE™), simethicone (sold under the trademarks Dow Corning Q7-2243 LVA™, Dow Corning Q7-2587™, SENTRY SIMETHICONE™), sodium alginate (sold under the trademarks KELCOSOL™, KELTONE™, PROTANAL™), sodium chloride (sold under the trademark ALBERGER™), sorbitol (sold under the trademarks LIPONEC 70-NC™, LIPONIC 76-NCV, MERITOL™, NEOSORB™, SORBIFIN™, SORBITOL INSTANT™, SORBOGEM™), starch (sold under the trademarks AYTEX P™, FLUFTEX W™, INSTANT PURE-COTE™, MELOJEL™, MERITENA PAYGEL 55™, PERFECTAMYL D6PH™, PURE-BIND™, PURE-COTE™, PURE-DENT™, PURE-GEL™, PURE-SET™, PURITY 21™, PURITY 826™, TABLET WHITE™), pregelatinized starch (sold under the trademarks INSTASTARCH™, LYCATAB C™, LYCATAB PGS™, MERIGEL™, NATIONAL 78-1551™, PHARMA-GEL™, PREJEL™, SEPISTAB ST 200™, SPRESS B820™, STARCH 1500 G™, TABLITZ™, UNIPURE LD™, UNIPURE WG220™), sucrose, trehalose and xylitol (sold under the trademarks KLINIT™, XYLIFM™, XYLITAB™, XYLISORB™, XYLITOLO™), or mixtures thereof.

The diluent/filler is preferably selected from microcrystalline cellulose and lactose, such as lactose anhydrous. Alternatively, any suitable diluent/filler can be used.

Lubricant

The presence of a lubricant is particularly preferred when the composition is a tablet as lubricants improve the tabletting process. Lubricants prevent composition ingredients from clumping together and from sticking to the tablet punches or capsule filling machine and improve flowability of the composition mixture. Accordingly, the total weight of the ibuprofen core may be comprised of about 0.1 to about 5 wt % lubricant, more preferably about 1 to about 3 wt % lubricant.

Suitable lubricants include calcium stearate (sold under the trademark HYQUAL™), glycerine monostearate (sold under the trademarks CAPMUL GMS-50™, CUTINA GMS™, IMWITOR™191 and 900, KESSCO GMS5™ LIPO GMS™ 410, 450 and 600, MYVAPLEX 600P™, MYVATEX™, PROTACHEM GMS-450™, RITA GMS™, STEPAN GMS™, TEGIN™, TEGIN™503 and 515, TEGIN 4100™, TEGIN M™, UNIMATE GMS™), glyceryl behenate (sold under the trademark COMPRITOL 888 ATO™), glyceryl palmitostearate (sold under the trademark PRECIROL ATO 5™), hydrogenated castor oil (sold under the trademarks CASTORWAX™, CASTPRWAX MP 70™, CASTORWAX MP 80™, CRODURE™, CUTINA HR™, FANCOL™, SIMULSOL 1293™), hydrogenated vegetable oil type I (sold under the trademarks AKOFINE™, LUBRITAB™, STEROTEX™, DYNASAN P60™, SOFTISAN 154™, HYDROCOTE™, LIPOVOL HS-K™, STEROTEX HM™), magnesium lauryl sulphate, magnesium stearate, medium-chain triglycerides (sold under the trademarks CAPTEX 300™, CAPTEX 355™, CRODAMOL GTC/C™, LABRAFAC CC™, MIGLYOL 810™, MIGLYOL 812™, MYRITOL™, NEOBEE M5™, NESATOL™, WAGLINOL 3/9280™), poloxamer (sold under the trademarks LUTROL™, MONOLAN™, PLURONIC™, SYNPERONIC™), polyethylene glycol (sold under the trademarks CARBOWAX™, CARBOWAX SENTRY™, LIPO™, LIPOXOL™, LUTROL E™, PLURIOL E™), sodium benzoate (sold under the trademark ANTIMOL™), sodium chloride (sold under the trademark ALBERGER™), sodium lauryl sulphate (sold under the trademarks ELFAN 240™, TEXAPON K1 2P™), sodium stearyl fumarate (sold under the trademark PRUV™), stearic acid (sold under the trademarks CRODACID E570™, EMERSOL™, HYSTRENE™, INDUSTRENE™, KORTACID 1895™, PRISTERENE™), talc (sold under the trademarks ALTAIC™, LUZENAC™, LUZENAC PHARMA™, MAGSIL OSMANTHUS™, MAGSIL STAR™, SUPERIORE™), sucrose stearate (sold under the trademark SURFHOPE SE PHARMA D-1803 F™) and zinc stearate (sold under the trademark HYQUAL™), or mixtures thereof.

Preferred lubricants include magnesium stearate and/or talc.

Glidant

Glidants improve the flowability of the composition. The composition may also comprise a glidant. Preferably, the total weight of the ibuprofen core is comprised of about 0 to about 3 wt %. glidant.

Suitable glidants include tribasic calcium phosphate (sold under the trademarks TRI-CAFOS™, TRI-CAL™, TRI-TAB™), calcium silicate, cellulose, powdered (sold under the trademarks ARBOCEL™, ELCEMA™, SANACEL™, SOLKA-FLOC™), colloidal silicon dioxide (sold under the trademarks AEROSIL™, CAB-O-SIL™, CAB-O-SIL M-5P™, WACKER HDK™), magnesium silicate, magnesium trisilicate, starch (sold under the trademarks AYTEX P™, FLUFTEX W™, INSTANT PURE-COTE™, MELOJEL™, MERITENA™, PAYGEL 55™, PERFECTAMYL D6PH™, PURE-BIND™, PURE-COTE™, PURE-DENT™, PURE-GEL™, PURE-SET™, PURITY 21™, PURITY 826™, TABLET WHITE™) and talc (sold under the trademarks ALTAIC™, LUZENAC™, LUZENAC PHARMA™, MAGSIL OSMANTHUS™, MAGSIL STAR™, SUPERIORE™), or mixtures thereof.

Preferred glidants are colloidal silicon dioxide and/or talc.

The outermost coating layer of the formulation may include a color coating to provide an aesthetic look. One example of the colorant is FD&C Blue No. 1, but other colorants may be used.

Formulation Example 1

To improve the stability of the ibuprofen and famotidine tablet, a formulation was prepared with a protective barrier coating between the ibuprofen core and the famotidine coating. Specifically, the formulation in Table 4, Formulation Example 1, includes a protective barrier coating of Opadry 03B28796 between the ibuprofen core and the famotidine outer drug coating.

TABLE 4

| Formulation Example 1 | |
| --- | --- |
| Material Name | Unit formula (mg) |
| Ibuprofen Core | |
| Ibuprofen (intragranular) | 800.00 |
| Microcrystalline Cellulose (intragranular) | 43.34 |
| Lactose Anhydrous (intragranular) | 48.44 |
| Povidone K 30 (intragranular)) | 25.00 |
| Purified water | Q.S |
| Croscarmellose sodium (extragranular) | 65.00 |
| Colloidal Silicon dioxide (extragranular) | 10.10 |
| Talc (extragranular) | 6.00 |
| Magnesium Stearate (extragranular) | 12.12 |
| Ibuprofen core tablet weight | 1010.00 |
| Barrier Coating (6% ± 0.5 w/w) | |
| Opadry 03B28796 | 60.60 |
| Purified water | Q.S |
| Barrier coated tablet weight | 1070.60 |
| Famotidine Drug coating (6% ± 0.5 w/w) | |
| Famotidine | 26.60 |
| Opadry 85F190000 | 36.42 |
| Purified water | Q.S. |
| Final tablet weight | 1133.62 |

A mixture of ibuprofen, microcrystalline cellulose and lactose was granulated using an aqueous dispersion of Povidone K30. The granules were then blended with croscarmellose sodium and colloidal silicon dioxide. The blend of granules was then lubricated with talc and magnesium stearate. The lubricated blend then was compressed to form ibuprofen tablets. The ibuprofen tablets then were coated with the Opadry coating followed by coating with the famotidine drug coating.

The resulting tablets were stored for fifteen days at 60° C. in an open container to evaluate the tablets under accelerated conditions and for one month at 40° C. and 75% relative humidity. Table 5 reports the famotidine-related compounds after storage under both conditions.

TABLE 5

Famotidine-related impurities of Example 1

| | | | Formulation Approach: Ibuprofen core tablets with barrier coating followed by famotidine drug coating | |
| --- | --- | --- | --- | --- |
| | | | Condition: | |
| Famotidine related compounds | Proposed Spec limits | Initial-RT | 60° C. 2 weeks Open exposure | 40° C./ 75% RH 1 Month Open exposure |
| Famotidine Amidine (RC-A) | NMT 0.2% | 0.02 | 0.56* | 0.27 |
| Famotidine dimer (RC-B) | NMT 0.3% | 0.009 | 0.04 | ND |
| Famotidine Sulfamoyl propanamide (RC-C) | NMT 0.5% | 0.04 | 0.36 | 14.83* |
| Famotidine Propanamide (RC-D) | NMT 0.5% | 0.07 | 0.14 | 1.43* |
| Famotidine disulfide (RC-E) | NMT 0.3% | ND | 0.02 | 0.13 |
| Famotidine Propionic acid (RC-F) | NMT 0.5% | 0.03 | 0.03 | 0.87* |
| Famotidine Sulfoxide | NMT 1.0% | ND | ND | 0.42 |
| Single max unspecified imp | NMT 0.2% | 0.07 | 0.10 | 0.20 |
| Total Impurity | 1.5% | 0.68 | 2.01 | 19.5* |

*Exceeds proposed specification limit

The stability data reported in Table 5 shows good stability at 60° C. with open exposure. However, the data shows that this formulation exhibits rapid and extensive famotidine degradation at 40° C./75% RH with open exposure. This is surprising because the formulation separates the famotidine active ingredient from the ibuprofen active ingredient by a protective barrier coating. The stability study at 40° C./75% RH with open exposure indicates that the drug product degradation and the degradation kinetics are faster in the presence of both increased heat and humidity in spite of the particular barrier coating selected in the example.

Further formulation trials were conducted to determine if different protective barrier coating materials between the ibuprofen core and the famotidine active layer coating and/or different coating materials used with the famotidine would provide improved stability. The formulations were made and stability studies conducted at 40° C./75% RH in open and closed conditions to screen for stable formulations and determine the characteristics of a suitable barrier coating material.

The formulations in Table 6, Formulation Examples 2 and 3, include a protective barrier coating of Acryl-EZE II-493Z180022 and hydroxypropyl methyl cellulose E3 Premium LV. Examples 2 and 3 differ in the use of the coating material used with the famotidine: Opadry 85F190000 (Example 2) and Opadry 03B28796 (Example 3). Example 1 included Opadry 85F190000 as the coating material used with the famotidine. Examples 2 and 3, therefore, compare the effect on stability of the coating material used with the famotidine.

TABLE 6

Formulation Examples 2 and 3

| Material Name | Example 2 Unit formula (mg) | Example 3 Unit formula (mg) |
|---|---|---|
| Ibuprofen Core | | |
| Ibuprofen (intragranular) | 800.00 | 800.00 |
| Microcrystalline Cellulose (intragranular) | 43.34 | 43.34 |
| Lactose Anhydrous (intragranular) | 48.44 | 48.44 |
| Povidone K 30 (intragranular) | 25.00 | 25.00 |
| Purified water | Q.S | Q.S |
| Croscarmellose sodium (extragranular) | 65.00 | 65.00 |
| Colloidal Silicon dioxide (extragranular) | 10.10 | 10.10 |
| Talc (extragranular) | 6.00 | 6.00 |
| Magnesium Stearate (extragranular) | 12.12 | 12.12 |
| Ibuprofen tablet weight | 1010.00 | 1010.00 |
| Barrier Coating (4% ± 0.5 w/w) | | |
| Acryl - EZE II-493Z180022 White | 32.32 | 32.32 |
| HPMC E3 premium LV | 8.08 | 8.08 |
| Purified water | Q.S. | Q.S. |
| Barrier coated tablet weight | 1050.40 | 1050.40 |
| Famotidine Drug coating (6% ± 0.5 w/w) | | |
| Famotidine | 26.60 | 26.60 |
| Opadry 85F190000 | 36.42 | — |
| Opadry 03B28796 | — | 36.42 |
| Purified water | Q.S. | Q.S. |
| Final tablet weight | 1113.42 | 1113.42 |

A mixture of ibuprofen, microcrystalline cellulose and lactose was granulated using an aqueous dispersion of Povidone K30. The granules were then blended with croscarmellose sodium and colloidal silicon dioxide. The blend of granules were then lubricated with talc and magnesium stearate. The lubricated blend then was compressed to form ibuprofen tablets. The ibuprofen tablets then were coated with the Acryl-EZE II and hydroxypropyl methyl cellulose coating followed by coating with the famotidine-Opadry drug coating.

The resulting tablets were stored for one month at 40° C. and 75% relative humidity at open and closed conditions. Formulation Example 3 was also stored under these conditions for three months in a closed condition. Table 7 reports the famotidine-related compounds after storage under this condition.

The stability data reported in Table 7 shows that the formulation of Example 3 exhibits better stability at 40° C./75% RH in open and closed conditions in comparison to the formulation of Example 2. However, famotidine impurity C was found to be slightly higher in the formulation of Example 3 at 3 months storage at 40° C./75% RH closed conditions.

Based on a comparison of Examples 1, 2 and 3, the inventors concluded that a combination of Acryl-EZE II-493Z180022 White and Opadry 03B28796 coatings will together provide a better, overall protective coating system to stabilize the drug product and control the impurity levels when stored for at least three months at 40° C. and 75% relative humidity. To test this conclusion, the inventors formulated additional tablets using a combination of Acryl-EZE II-493Z180022 White and Opadry 03B28796 as the protective barrier coating between the ibuprofen core and the famotidine active layer coating to stabilize the drug product.

TABLE 7

Famotidine-related impurities of Examples 2 and 3

| | | Example 2 | | | Example 3 | | | |
|---|---|---|---|---|---|---|---|---|
| | | Formulation Approach | | | | | | |
| | | Ibuprofen Core Tablets with barrier coating followed by Famotidine drug coating | | | Ibuprofen Core Tablets with barrier coating followed by Famotidine drug coating | | | |
| | | Stability Condition | | | | | | |
| | | | 40° C./75% RH | | | 40° C./75% RH | | |
| Famotidine related compounds | Proposed Spec limits | Initial-RT | 1 Month Open | 1 Month Close | Initial-RT | 1 Month Open | 1 Month Close | 3 Month Close |
|---|---|---|---|---|---|---|---|---|
| 1 Famotidine Amidine (RC-A) | NMT 0.2% | 0.03 | 0.07 | 0.04 | 0.02 | 0.04 | 0.04 | 0.02 |
| 2 Famotidine dimer (RC-B) | NMT 0.3% | 0.005 | ND | ND | 0.01 | ND | ND | ND |
| 3 Famotidine Sulfamoyl propanamide (RC-C) | NMT 0.5% | 0.04 | 13.58* | 0.52* | 0.08 | 3.51* | 0.21 | 0.69* |
| 4 Famotidine Propanamide (RC-D) | NMT 0.5% | 0.06 | 1.14* | 0.11 | 0.06 | 0.33 | 0.07 | 0.19 |
| 5 Famotidine disulfide (RC-E) | NMT 0.3% | ND | 0.01 | 0.009 | 0.007 | 0.02 | 0.01 | 0.01 |
| 6 Famotidine Propionic acid (RC-F) | NMT 0.5% | 0.02 | 1.25* | 0.04 | 0.02 | 0.34 | 0.02 | 0.09 |
| 7 Famotidine Sulfoxide | NMT 1.0% | ND | 0.41 | 0.13 | ND | 0.12 | 0.18 | 0.17 |
| 8 Single max unspecified imp | NMT 0.2% | 0.07 | 0.14 | 0.05 | 0.20 | 0.04 | 0.06 | 0.08 |
| Total Impurity | 1.5% | 0.45 | 17.12* | 1.14 | 0.78 | 4.8* | 0.92 | 1.57* |

*Exceeds proposed specification limit

Formulation Example 3 is configured to test the combination of a first protective barrier coating of Acryl-EZE II-493Z180022 White, a second protective barrier coating of Opadry 03B28796 and a famotidine active ingredient layer coating that contains Opadry 85F190000.

TABLE 7

Formulation Example 4

| Material Name | Formulation Example 4 Unit formula (mg) |
|---|---|
| Ibuprofen Core | |
| Ibuprofen (intragranular) | 800.00 |
| Microcrystalline Cellulose (intragranular) | 43.34 |
| Lactose Anhydrous (intragranular) | 48.44 |
| Povidone K 30 (intragranular) | 25.00 |
| Purified water | Q.S. |
| Croscarmellose sodium (extragranular) | 65.00 |
| Colloidal Silicon dioxide (extragranular) | 10.10 |
| Talc (extragranular) | 6.00 |
| Magnesium Stearate (extragranular) | 12.12 |
| Ibuprofen tablet weight | 1010.00 |
| Barrier Coating (First Layer) (3% ± 0.5 w/w) | |
| Acryl - EZE II-493Z180022 White | 24.24 |
| HPMC E3 premium LV | 6.06 |
| Purified water | Q.S |
| Barrier coated tablet weight | 1040.30 |
| Barrier Coating (Second Layer) (4% ± 0.5 w/w) | |
| Opadry 03B28796 | 41.61 |
| Purified water | Q.S. |
| Second Barrier coated Tablets weight (mg) | 1081.91 |
| Famotidine Drug coating (6% ± 0.5 w/w) | |
| Famotidine | 26.60 |
| Opadry 85F190000 | 36.49 |
| Purified water | Q.S. |
| Final tablet weight | 1145.0 |

The coating materials used in Formulation Example 4 have the following compositions. The amount in each tablet of Formulation Example 4 also are included in Tables 8-10.

Table 8 lists the components and amounts of the components in the Acryl-EZE II acrylic enteric polymer coating system. The coating system is provided as a ready mix powder.

TABLE 8

Acryl-EZE II Aqueous Acrylic Enteric System 493Z180022 White

| Material Name | Functional Category | mg/unit |
|---|---|---|
| Methacrylic acid and ethyl acrylate copolymer (Type A) | Enteric coating polymer | 13.33 |
| Talc | Glidant | 4.80 |
| Titanium Dioxide | Opacifier | 3.15 |
| Poloxamer 407 | Surfactant | 1.60 |
| Calcium Silicate | Anticaking agent | 0.97 |
| Sodium Bicarbonate | Alkaliser | 0.27 |
| Sodium Lauryl Sulfate | Surfactant | 0.12 |
| Total quantity of Acryl - EZE II, 493Z180022 White per tablet | | 24.24 |

Although the Acryl-EZE II uses a methacrylic acid and ethyl acrylate copolymer, other polymer systems are expected to provide suitable functionality. Such polymer systems include methacrylic acid, methyl methacrylate (1:1) (Eudragit L100) and methacrylic acid, methyl methacrylate (1:2) (Eudragit S100). As reported in the pharmaceutical formulation literature, these three polymers are chemically similar in that they are all anionic polymethacrylate polymers that contain methacrylic acid functional groups, which dissociate and render the polymer soluble at the higher pH of the small intestine (from pH 5.5 to 7.0). As such, each is expected to suitably function for their intended purpose in the same or similar amounts.

Table 9 lists the components and amounts of the components in the Opadry Complete film coating system 03B28796. The coating system is provided as a ready mix powder.

TABLE 9

| Opadry 03B28796 Coating System | | |
| --- | --- | --- |
| Material Name | Functional Category | mg/unit |
| Hypromellose 6 m pas | Film forming agent | 26.01 |
| Titanium Dioxide | Opacifier | 13.00 |
| Macrogol/PEG (MW 400) | Plasticizer | 2.60 |
| Total quantity of Opadry Complete film coating system 03B28796 per tablet | | 41.61 |

Table 10 lists the components and amounts of the components in the Opadry Clear coating system 85F190000. The coating system is provided as a ready mix powder.

TABLE 10

| Opadry 85F190000 Clear Coating System | | |
| --- | --- | --- |
| Material Name | Functional Category | mg/unit |
| Polyvinyl Alcohol | Film forming agent | 19.34 |
| Macrogol/PEG (MW3350) | Plasticizer | 9.85 |
| Talc | Glidant | 7.30 |
| Total quantity of Opadry 85F190000 clear per tablet | | 36.49 |

Process for Preparation of Tablets:

The tablets of formulation Example 4, using the active ingredients and coating systems of Tablets 7-10, were prepared by a wet granulation manufacturing process that involves the manufacturing process unit operations of sifting, wet granulation, drying, milling, blending, compression and coating as, set out below:

A. Intragranular Sifting (Equipment: Mechanical sifter)
  1. Weight all the ingredients individually as per the weighing record.
  2. Co-sift the intragranular materials (ibuprofen, microcrystalline cellulose, and lactose anhydrous) through a 20 #mesh.
B. Granulation (Equipment: Rapid Mixing Granulator [RMG])
  3. Dissolve the povidone in water under stirring.
  4. Granulate the dry mix content of Step No. 2 in RMG using the binder solution of Step No. 3.
C. Drying (Equipment: FBP/Drier)
  5. Dry the wet mass of Step No. 4 in a fluid bed drier at 60° C.±10° C. until the desired LOD is achieved.
D. Milling (Equipment: Cone mill with suitable screen size)
  6. Mill the dried granules of Step No. 5 in a co-mill fitted with a suitable screen at the desired rpm.
E. Extragranular Sifting (Equipment: Mechanical sifter)
  7. Co-sift the extragranular materials (croscarmellose sodium, colloidal silicon dioxide, talc and magnesium stearate) through a 30 #mesh.
F. Blending (Equipment: V blender)
  8. Load the milled granules of Step No. 6 and the sifted material of Step No. 7 into a suitable V-Cone blender and blend for 15 minutes at 18 RPM.
G. Compression (Equipment: Compression machine)
  9. Compress the final ibuprofen blend of Step No. 8 into core tablets using suitable tooling.
H. Barrier Coating (First Layer) (Coating machine)
  10 Disperse the required quantity of Acryl-EZE in water under stirring.
  11. Add hydroxypropylmethylcellulose (HPMC) E3 premium LV to the solution of Step No. 10 under stirring and continue the stirring for about 45 minutes.
  12. Transfer the core tablets from Step No. 9 to a coating pan and coat the tablets until obtaining a weight build-up of 3-4%.
I. Barrier Coating (Second Layer) (Coating machine)
  13. Disperse the required quantity of Opadry Complete film coating system 03B28796 in water under stirring and continue the stirring for about 45 minutes.
  14. Transfer the barrier coated tablets of Step No. 12 to the coating pan and coat the tablets until achieving a weight build-up of 4±0.5%.
J. Famotidine Drug Layering coating (Coating machine)
  15. Disperse the required quantity of Opadry 85F190000 Clear in water under stirring and continue the stirring for about 30 minutes.
  16. Add the famotidine to the solution of Step No. 15 under stirring and homogenize the dispersion for 20 minutes at a suitable rpm.
  17. Transfer the barrier coated tablets of Step No. 14 to the coating pan and coat the tablets until get achieving a weight build-up of 5.82±0.5%.

The tablets of Formulation Example 4 were stored at 40C and 75% relative humidity in open containers for one month and closed containers for three months and tested for related compounds to analyse stability. The results are provided in Table 11 (famotidine related impurities) and Table 12 (ibuprofen related impurities).

TABLE 11

| Famotidine Related Impurities | | | | | | |
| --- | --- | --- | --- | --- | --- | --- |
| | | | Formulation Approach Ibuprofen Core Tablets with two barrier coating followed by Famotidine drug coating (Example 4) Stability Condition | | | |
| | | | 40° C./75% RH | | | |
| Famotidine related compounds (%) | Proposed Spec limits | Initial-RT | 1 Month Open | 1 Month Close | 2 Month Close | 3 Month Close |
| Famotidine Amidine (RC-A) | NMT 0.2% | 0.01 | ND | ND | ND | 0.01 |
| Famotidine dimer (RC-B) | NMT 0.3% | ND | ND | ND | ND | ND |
| Famotidine Sulfamoyl propanamide (RC-C) | NMT 0.5% | 0.05 | 0.86 | 0.07 | 0.09 | 0.08 |
| Famotidine Propanamide (RC-D) | NMT 0.5% | 0.05 | 0.12 | 0.05 | 0.07 | 0.07 |
| Famotidine disulfide (RC-E) | NMT 0.3% | ND | 0.01 | 0.01 | 0.01 | 0.01 |

TABLE 11-continued

Famotidine Related Impurities

Formulation Approach
Ibuprofen Core Tablets with two barrier
coating followed by Famotidine drug
coating (Example 4)
Stability Condition

40° C./75% RH

| Famotidine related compounds (%) | Proposed Spec limits | Initial-RT | 1 Month Open | 1 Month Close | 2 Month Close | 3 Month Close |
|---|---|---|---|---|---|---|
| Famotidine Propionic acid (RC-F) | NMT 0.5% | 0.01 | 0.09 | 0.02 | 0.03 | 0.01 |
| Famotidine Sulfoxide | NMT 1.0% | 0.17 | 0.37 | 0.26 | 0.09 | 0.15 |
| Single max unspecified imp | NMT 0.2% | 0.06 | 0.11 | 0.07 | 0.05 | 0.04 |
| Total Impurity | 1.5% | 0.59 | 2.07 | 0.80 | 0.76 | 0.69 |

TABLE 12

Ibuprofen Related Impurities

Formulation Approach
Ibuprofen Core Tablets with two barrier
coating followed by Famotidine drug
coating (Example 4)
Stability Condition

40° C./75% RH

| Ibuprofen related compounds (%) | Proposed Spec limits | Initial-RT | 1 Month Open | 1 Month Close | 2 Month Close | 3 Month Close |
|---|---|---|---|---|---|---|
| 1 Impurity J | NMT 0.2% | 0.00 | 0.00 | 0.00 | 0.00 | 0.00 |
| 2 Single max unspecified imp | NMT 0.2% | 0.02 | 0.02 | 0.02 | 0.02 | 0.02 |
| Total Impurity | 1.5% | 0.04 | 0.04 | 0.05 | 0.05 | 0.05 |

Based on the observed stability data, the formulation composition of Example 4 with a combination of Acryl-EZE II-493Z180022 White and Opadry 03B28796 as the protective barrier coatings between the ibuprofen core and the famotidine active layer coating exhibits a stability that meets the proposed specifications when stored for at three months at 40° C. and 75% relative humidity.

Based on achieving the desired stability results, the tablets of Example 4 were tested for dissolution along with ibuprofen-famotidine tablets (sold under the trademark Duexis®), the brand product of famotidine and ibuprofen. The dissolution results are reported below in Table 13.

TABLE 13

Comparative Dissolution Profile of the
Tablets of Example 4 and Duexis Tablets

Name of sample:

DUEXIS Tablets 800/26.6 mg     Test Product (Example 4)
Media:
pH 7.2 Phosphate Buffer (OGD), 900 mL, Paddle, 50 rpm
% Drug Release (% RSD)

| Time (minutes) | Famotidine | Ibuprofen | Famotidine | Ibuprofen |
|---|---|---|---|---|
| 5 | 0 | 31 (17.3) | 41 (13.7) | 0 |
| 10 | 60 (17.8) | 90 (2.1) | 58 (16.0) | 17 (23.7) |
| 15 | 77 (13.5) | 97 (1.1) | 72 (16.3) | 54 (9.9) |
| 20 | 83 (11.8) | 98 (0.9) | 81 (9.5) | 83 (6.8) |
| 30 | 89 (9.5) | 99 (0.7) | 86 (8.1) | 98 (0.6) |
| 45 | 92 (7.9) | 99 (0.6) | 90 (6.4) | 99 (0.4) |
| 60 | 94 (7.1) | 99 (0.5) | 93 (5.5) | 100 (0.5) |

The dissolution testing of the tablets of Example 4 demonstrate a sufficient and acceptable level of similarity to the dissolution of the ibuprofen-famotidine tablets (sold under the trademark Duexis® tablets). Of note, at five minutes in the test system, the protective enteric coating had prevented the ibuprofen from releasing. This is a different result from that disclosed in U.S. Pat. No. 8,067,451, which describes the barrier layer as retarding the release of active ingredient, e.g., ibuprofen, by less than 5 minutes.

Based on the successful stability and dissolution results, the formulation of Example 4 was reproduced in a second batch (Example 5) according to the process used to make the tablets of Example 4. The tablets of Example 5 were subject to the same dissolution testing reported in Table 13 (pH 7.2, Table 14) as well as at pH 6.8 (Table 15), pH 4.5 (Table 16) and 0.1 N HCl (Table 17).

TABLE 14

Comparative Dissolution Profile of the Tablets of Example 5 and Duexis Tablets at pH 7.2

Name of sample:

DUEXIS Tablets 800/26.6 mg    Test Product (Example 5)
Media:
pH 7.2 Phosphate Buffer (OGD), 900 mL, Paddle, 50 rpm
Number of units:

| Time | 6 units | | 6 units | |
|---|---|---|---|---|
| | % Drug Release (% RSD) | | | |
| (minutes) | Famotidine | Ibuprofen | Famotidine | Ibuprofen |
| 5 | 0 | 31 (17.3) | 30 (12.6) | 0 |
| 10 | 60 (17.8) | 90 (2.1) | 53 (19.4) | 25 (61.3) |
| 15 | 77 (13.5) | 97 (1.1) | 67 (11.8) | 66 (21.5) |
| 20 | 83 (11.8) | 98 (0.9) | 75 (10.2) | 89 (5.0) |
| 30 | 89 (9.5) | 99 (0.7) | 82 (8.4) | 95 (1.4) |
| 45 | 92 (7.9) | 99 (0.6) | 88 (7.1) | 97 (1.1) |
| 60 | 94 (7.1) | 99 (0.5) | 92 (6.9) | 98 (1.1) |

The dissolution testing of the tablets of Example 5 at pH 7.2 reported in Table 14 demonstrate a sufficient and acceptable level of similarity to the dissolution of the ibuprofen-famotidine tablets (sold under the trademark Duexis® tablets). Of note, at five minutes in the test system, the protective enteric coating had prevented the ibuprofen from being released.

TABLE 15

Comparative Dissolution Profile of the Tablets of Example 5 and Duexis Tablets at pH 6.8

Name of sample:

DUEXIS Tablets 800/26.6 mg    Test Product (Example 5)
Media:
pH 6.8 Phosphate Buffer, 900 mL, Paddle, 50 rpm
Number of units:

| Time | 6 units | | 6 units | |
|---|---|---|---|---|
| | % Drug Release (% RSD) | | | |
| (minutes) | Famotidine | Ibuprofen | Famotidine | Ibuprofen |
| 5 | 0 | 12 (31.6) | 27 (16.1) | 0 |
| 10 | 64 (18.3) | 75 (3.8) | 51 (14.4) | 13 (28.7) |
| 15 | 80 (11.0) | 92 (1.8) | 68 (7.2) | 56 (12.5) |
| 20 | 84 (9.1) | 96 (1.7) | 80 (8.7) | 87 (2.4) |
| 30 | 88 (8.3) | 98 (1.8) | 87 (7.3) | 95 (1.1) |
| 45 | 90 (7.8) | 98 (1.7) | 94 (5.3) | 97 (0.8) |
| 60 | 91 (7.5) | 98 (1.8) | 97 (4.6) | 97 (0.6) |

The dissolution testing of the tablets of Example 5 at pH 6.8 reported in Table 15 demonstrate a sufficient and acceptable level of similarity to the dissolution of the ibuprofen-famotidine tablets (sold under the trademark Duexis® tablets). Of note, at five minutes in the test system, the protective enteric coating had prevented the ibuprofen from being released.

TABLE 16

Comparative Dissolution Profile of the Tablets of Example 5 and Duexis Tablets at pH 4.5

Name of sample:

DUEXIS Tablets 800/26.6 mg    Test Product (Example 5)
Media:
pH 4.5 Acetate buffer, 900 mL, Paddle, 50 rpm
Number of units:

| Time | 6 units | | 6 units | |
|---|---|---|---|---|
| | % Drug Release (% RSD) | | | |
| (minutes) | Famotidine | Ibuprofen | Famotidine | Ibuprofen |
| 5 | 1 | 0 | 43 (11.0) | 0 |
| 10 | 82 (17.3) | 1 (39.6) | 68 (7.5) | 0 |
| 15 | 91 (8.5) | 8 (8.3) | 78 (4.9) | 0 |
| 20 | 93 (7.9) | 11 (2.8) | 84 (3.7) | 0 |
| 30 | 94 (7.9) | 11 (3.2) | 93 (3.6) | 6 (16.0) |
| 45 | 96 (7.0) | 10 (1.9) | 97 (4.5) | 11 (17.1) |
| 60 | 97 (6.2) | 10 (1.0) | 98 (4.6) | 12 (4.0) |
| Infinity | 103 (2.1) | 10 (1.1) | 100 (4.5) | 11 (1.4) |

The dissolution testing of the tablets of Example 5 at pH 4.5 reported in Table 16 demonstrate a sufficient and acceptable level of similarity to the dissolution of the ibuprofen-famotidine tablets (sold under the trademark Duexis® tablets). Of note, at five minutes and through at least twenty minutes in the test system, the protective enteric coating had prevented the ibuprofen from being released.

TABLE 17

Comparative Dissolution Profile of the Tablets of Example 5 and Duexis Tablets at 0.1N HCl Name of sample:

DUEXIS Tablets 800/26.6 mg    Test Product
Media:
0.1N HCl, 900 mL, Paddle, 50 rpm
Condition:

| | RT | | RT | |
|---|---|---|---|---|
| | Famotidine | Ibuprofen | Famotidine | Ibuprofen |
| 5 | 0 | 1 | 76 (8.8) | 0 |
| 10 | 73 (41.6) | 4 (13.7) | 87 (11.9) | 0 |
| 15 | 94 (12.0) | 6 (6.8) | 94 (10.2) | 0 |
| 20 | 96 (9.7) | 7 (5.8) | 96 (9.5) | 0 |
| 30 | 98 (7.6) | 7 | 97 (1.0) | 0 |
| 45 | 100 (5.6) | 7 | 97 (1.3) | 0 |
| 60 | 101 (4.0) | 7 | 97 (2.5) | 6 |
| Infinity | 104 (1.1) | 7 | 97 (2.5) | 6 |

The dissolution testing of the tablets of Example 5 in 0.1N HCl reported in Table 17 demonstrate a sufficient and acceptable level of similarity to the dissolution of the ibuprofen-famotidine tablets (sold under the trademark Duexis® tablets). Of note, at five minutes and throughout the entirety that the tablets were in the test system, the protective enteric coating had prevented the ibuprofen from being released.

Formulation Example 6 of Table 18 is designed to test the combination of Example 4 but with a different first protective barrier coating. Rather than the Acryl-EZE II-493Z180022 White of Example 4, Example 6 includes Eudragit S100.

TABLE 18

Formulation Example 6

| Material Name | Formulation Example 64 Unit formula (mg) |
|---|---|
| Ibuprofen Core | |
| Ibuprofen (intragranular) | 800.00 |
| Microcrystalline Cellulose (intragranular) | 43.34 |
| Lactose Anhydrous (intragranular) | 48.44 |
| Povidone K 30 (intragranular) | 25.00 |
| Purified water | Q.S. |
| Croscarmellose sodium (extragranular) | 65.00 |
| Colloidal Silicon dioxide (extragranular) | 10.10 |
| Talc (extragranular) | 6.00 |
| Magnesium Stearate (extragranular) | 12.12 |
| Ibuprofen tablet weight | 1010.00 |
| Barrier Coating (First Layer) (3.5% ± 0.5 w/w) | |
| Eudragit S100 | 15.15 |
| Ammonia solution | Q.S |
| Triethyl citrate | 7.58 |
| Talc | 7.58 |
| HPMC E3 premium LV | 6.06 |
| Purified water | Q.S |
| Barrier coated tablet weight | 1046.37 |
| Barrier Coating (Second Layer) (4% ± 0.5 w/w) | |
| Opadry 03B28796 | 41.85 |
| Purified water | Q.S. |
| Second Barrier coated Tablets weight (mg) | 1088.22 |
| Famotidine Drug coating (6% ± 0.5 w/w) | |
| Famotidine | 26.60 |
| Opadry 85F190000 | 36.49 |
| Purified water | Q.S. |
| Final tablet weight | 1151.3 |

The tablets of Formulation Example 6 were stored at 40° C. and 75% relative humidity in closed containers for three months and tested for famotidine-related compounds to analyse stability. The results are provided in Table 19 (famotidine related impurities).

TABLE 19

Famotidine Related Impurities
Famotidine Related Substances

| | Batch No Example 6 (Formulation with Eudragit S100) | | |
|---|---|---|---|
| Condition | RT | 1 M 40° C./ 75% RH | 3 M 40° C./ 75% RH |
| Sulfoxide | 0.17 | 0.31 | 0.34 |
| RC D | 0.01 | 0.02 | 0.03 |
| RC C | 0.03 | 0.03 | 0.04 |
| RC F | 0.03 | 0.04 | 0.01 |
| RC A | 0.003 | 0.002 | 0.01 |
| RC E | ND | 0.004 | 0.01 |
| Single maximum unknown | 0.05 | 0.04 | 0.07 |
| Total | 0.38 | 0.61 | 0.80 |

Based on the observed stability data, the formulation composition of Example 6 with a combination of Eudragit S100 and Opadry 03B28796 as the protective barrier coatings between the ibuprofen core and the famotidine active layer coating exhibits a stability that meets the proposed specifications when stored for at three months at 40° C. and 75% relative humidity. As such, the inventors have shown that either a methacrylic acid/methyl methacrylate coating system or a methacrylic acid/ethyl acrylate copolymer coating system provides a stable ibuprofen and famotidine composition.

Based on the stability data, the inventors have developed a stable ibuprofen and famotidine fixed dose combination tablet that avoids instability related to the interactions between ibuprofen and famotidine. Based on the dissolution data, the use of an enteric polymer in the tablet delays the release of the ibuprofen from the tablet for at least five minutes and matches the release profile ibuprofen-famotidine tablets (sold under the trademark of Duexis®).

What is claimed:

1. A solid, pharmaceutical composition in compressed tablet form comprising:
   a core tablet comprising granules comprising about 800 mg of ibuprofen, from about 45 mg to about 120 mg of intragranular disintegrant and diluent/filler, from about 15 mg to about 35 mg of an intragranular binder, from about 50 to about 120 mg of extragranular disintegrant, and from about 15 mg to about 55 mg of extragranular glidant and lubricant;
   a pair of protective barrier coatings surrounding the ibuprofen core tablet, wherein a first coating comprises a copolymer selected from about 8 mg to about 40 mg of a methacrylic acid and ethyl acrylate copolymer having a molar ratio of methacrylic acid to ethyl acrylate of 1:1 or a methacrylic acid and methyl methacrylate copolymer having a molar ratio of methacrylic acid to methyl methacrylate of 1:2, from about 0.1 mg to about 1.0 mg of surfactant selected from the group consisting of poloxamer, sodium lauryl sulfate and mixtures thereof, from about 2 mg to about 20 mg of hydroxypropyl methylcellulose, from about 3 mg to about 15 mg of glidant, from about 2 mg to about 10 mg of opacifier and optional anticaking agent and alkalizer, and a second coating comprises from about 10 mg to about 60 mg of hydroxypropyl methylcellulose, from about 6 mg to about 30 mg of opacifier and from about 1.5 mg to about 6.0 mg of plasticizer; and
   an outermost coating comprising about 26.6 mg of famotidine, from about 15 mg to about 70 mg of polyvinyl alcohol, from about 4.0 mg to about 20 mg of plasticizer, and from about 6 mg to about 35 mg of glidant.

2. The solid pharmaceutical composition of claim 1, wherein the first coating is in contact with the ibuprofen core tablet and the second coating surrounds the first coating.

3. The solid pharmaceutical composition of claim 1, wherein the second coating is in contact with the ibuprofen core tablet and the first coating surrounds the second coating.

4. The solid pharmaceutical composition of claim 1, wherein the surfactant in the first coating comprises one or more of poloxamer and sodium lauryl sulfate.

5. The solid pharmaceutical composition of claim 1, wherein the first coating further comprises one or more of talc, titanium dioxide, poloxamer, calcium silicate, sodium bicarbonate and sodium lauryl sulfate.

6. The solid pharmaceutical composition of claim 1, wherein the plasticizer in the second coating comprises polyethylene glycol.

7. The solid pharmaceutical composition of claim 1, wherein the outermost coating comprises talc as the glidant.

8. The solid pharmaceutical composition of claim 1, wherein the plasticizer in the outermost coating comprises polyethylene glycol.

9. The solid pharmaceutical composition of claim 1, wherein the composition does not release ibuprofen from the composition within five minutes when the tablet is subjected to dissolution testing in a pH 7.2 phosphate buffer, 900 ml, and a paddle rotation speed of 50 rpm.

10. The solid pharmaceutical composition of claim 1, wherein the composition does not release ibuprofen from the composition within fifteen minutes when the tablet is subjected to dissolution testing in a pH 4.5 acetate buffer, 900 ml, and a paddle rotation speed of 50 rpm.

11. A solid, pharmaceutical composition in compressed tablet form comprising:
 a core tablet comprising granules comprising about 800 mg of ibuprofen, from about 45 mg to about 120 mg of an intragranular combination of microcrystalline cellulose and lactose, from about 15 mg to about 35 mg of povidone, from about 50 to about 120 mg of extragranular croscarmellose sodium, and from about 15 mg to about 55 mg of a combination of extragranular colloidal silicon dioxide, talc and magnesium stearate;
 a pair of protective barrier coatings surrounding the ibuprofen core tablet, wherein a first coating comprises from about 2 mg to about 20 mg of hydroxypropyl methylcellulose, from about 8 mg to about 40 mg of a methacrylic acid and ethyl acrylate copolymer having a molar ratio of methacrylic acid to ethyl acrylate of 1:1 or a methacrylic acid and methyl methacrylate copolymer having a molar ratio of methacrylic acid to methyl methacrylate of 1:2, from about 3 mg to about 15 mg of talc, from about 2 mg to about 10 mg of titanium dioxide, from about 1 mg to about 5.0 mg of a combination of poloxamer and sodium lauryl sulfate, and from about 2.0 mg to 15 mg of a combination of an optional anticaking agent and alkalizer;
 the second coating comprises from about 10 mg to about 60 mg of hydroxypropyl methylcellulose, from about 6 mg to about 30 mg of titanium dioxide and from about 1.5 mg to about 6.0 mg of polyethylene glycol; and
 the outermost coating comprises about 26.6 mg of famotidine, from about 15 mg to about 70 mg of polyvinyl alcohol, from about 4.0 mg to about 20.0 mg of polyethylene glycol, and from about 6 mg to about 35 mg of talc.

12. A solid, pharmaceutical composition in compressed tablet form comprising:
 a core tablet comprising granules comprising about 800 mg of ibuprofen, from about 45 mg to about 120 mg of intragranular disintegrant and diluent/filler, and from about 15 mg to about 35 mg of binder, from about 50 to about 120 mg of extragranular disintegrant, and from about 15 mg to about 55 mg of extragranular glidant and lubricant;
 a pair of protective barrier coatings surrounding the ibuprofen core tablet, wherein a first coating comprises a methacrylic acid and ethyl acrylate copolymer, from about 0.1 mg to about 1.0 mg of a surfactant selected from the group consisting of poloxamer, sodium lauryl sulfate and mixtures thereof, and from about 2 mg to about 20 mg of hydroxypropyl methylcellulose, from about 3 mg to about 15 mg of glidant, from about 2 mg to about 10 mg of opacifier, and a second coating comprises from about 10 mg to about 60 mg of hydroxypropyl methylcellulose, from about 15 mg to about 70 mg of opacifier, and from about 1.5 mg to about 6.0 mg of a plasticizer; and
 an outermost coating comprising famotidine, from about 15 mg to about 70 mg of polyvinyl alcohol, from about 6 mg to about 35 mg of glidant, and from about 4.0 mg to about 20 mg of a plasticizer,
 wherein the composition does not release ibuprofen from the composition within five minutes when the tablet is subjected to dissolution testing in a pH 7.2 phosphate buffer, 900 ml, and a paddle rotation speed of 50 rpm.

13. The solid pharmaceutical composition of claim 12, wherein the binder is selected from the group consisting of povidone, hypromellose, hydroxypropyl cellulose, methylcellulose, ethyl-cellulose, pregelatinized maize starch, gelatine, and mixtures thereof.

14. The solid pharmaceutical composition of claim 12, wherein the surfactant in the first coating is poloxamer or sodium lauryl sulfate.

15. The solid pharmaceutical composition of claim 13, wherein the plasticizer in the second coating comprises polyethylene glycol.

16. A process for preparing a solid, pharmaceutical composition of ibuprofen and famotidine in the form of a compressed tablet, the process comprising:
 preparing granules of ibuprofen and one or more pharmaceutically acceptable excipients selected from intragranular disintegrants, diluent/filler and binders;
 blending the granules with one or more extragranular disintegrants, glidants and lubricants;
 compressing the blend to form ibuprofen core tablets, wherein the ibuprofen core tablet comprises from about 800 mg of ibuprofen, from about 45 mg to about 120 mg of intragranular disintegrant and diluent/filler, from about 15 mg to about 35 mg of the binder, from about 50 to about 120 mg of the extragranular disintegrant, and from about 15 mg to about 55 mg of the extragranular glidant and lubricant;
 preparing coated ibuprofen core tablets by coating the ibuprofen core tablets with a pair of protective barrier coatings, wherein a first coating comprises from about 8 mg to about 40 mg of a methacrylic acid and ethyl acrylate copolymer, from about 3 mg to about 15 mg of glidant, from about 2 mg to about 10 mg of opacifier, from about 0.1 mg to about 1.0 mg of a surfactant selected from the group consisting of poloxamer and sodium lauryl sulfate, optional anticaking agent and alkalizer, and from about 2 mg to about 20 mg of hydroxypropyl methylcellulose,
 and a second coating comprises from about 10 mg to about 60 mg of hydroxypropyl methylcellulose, from about 6 mg to about 30 mg of opacifier and from about 1.5 mg to about 6.0 mg of a plasticizer; and
 coating the coated ibuprofen core tablets with an outermost coating comprising about 26.6 mg of famotidine, from about 15 mg to about 70 mg of polyvinyl alcohol, from about 4.0 mg to about 20 mg of a plasticizer, and from about 6 mg to about 35 mg of glidant.

17. The process of claim 16, wherein the first coating is in contact with the ibuprofen core tablet and the second coating surrounds the first coating or the second coating is in contact with the ibuprofen core tablet and the first coating surrounds the second coating.

18. The process of claim 16, wherein the surfactant in the first coating is poloxamer or sodium lauryl sulfate.

* * * * *